US008663949B2

(12) United States Patent
Schultz

(10) Patent No.: US 8,663,949 B2
(45) Date of Patent: Mar. 4, 2014

(54) FERMENTATION METHOD

(75) Inventor: Michael Anthony Schultz, Glen Ellyn, IL (US)

(73) Assignee: LanzaTech New Zealand Limited, Auckland (NZ)

( * ) Notice: Subject to any disclaimer, the term of this patent is extended or adjusted under 35 U.S.C. 154(b) by 0 days.

(21) Appl. No.: 13/330,568

(22) Filed: Dec. 19, 2011

(65) Prior Publication Data

US 2012/0156739 A1 Jun. 21, 2012

Related U.S. Application Data

(60) Provisional application No. 61/424,893, filed on Dec. 20, 2010.

(51) Int. Cl.
*C12P 1/00* (2006.01)
*C12P 7/54* (2006.01)
*C12P 7/16* (2006.01)
*C12P 7/06* (2006.01)
*C12P 7/08* (2006.01)

(52) U.S. Cl.
USPC ............. 435/41; 435/140; 435/160; 435/161; 435/163

(58) Field of Classification Search
None
See application file for complete search history.

(56) References Cited

U.S. PATENT DOCUMENTS

| 4,792,441 | A | 12/1988 | Wang et al. |
| 5,173,429 | A | 12/1992 | Gaddy et al. |
| 5,593,886 | A | 1/1997 | Gaddy |
| 6,368,819 | B1 | 4/2002 | Gaddy et al. |
| 7,078,201 | B2 | 7/2006 | Burmaster |
| 2006/0112639 | A1* | 6/2006 | Nick et al. .................. 48/198.1 |
| 2009/0203100 | A1 | 8/2009 | Simpson et al. |
| 2010/0105115 | A1 | 4/2010 | Simpson et al. |
| 2010/0133472 | A1 | 6/2010 | Han |

FOREIGN PATENT DOCUMENTS

| EP | 117309 A1 | 9/1984 |
| WO | WO 98/00558 | 1/1998 |
| WO | WO 00/68407 | 11/2000 |
| WO | WO 02/08438 | 1/2002 |
| WO | WO 2007/117157 | 10/2007 |
| WO | WO 2008/115080 | 9/2008 |
| WO | WO 2009/022925 | 2/2009 |
| WO | WO 2009/064200 | 5/2009 |
| WO | WO 2009058028 A1 * | 5/2009 |
| WO | WO 2010112501 A1 * | 10/2010 |

OTHER PUBLICATIONS

Abrini, J. et al., (1994). Clostridium autoethanogenum, Sp-Nov, an Anaerobic bacterium that produces ethanol from carbon monoxide. Archives of Microbiology, 161(4), 345-351.

* cited by examiner

*Primary Examiner* — Chris R Tate
*Assistant Examiner* — Douglas F White
(74) *Attorney, Agent, or Firm* — Frank S Molinaro

(57) ABSTRACT

This invention relates to the integration of an ammonia production process with a fermentation process to produce products such as alcohols and/or acids in addition to ammonia. In a specific embodiment, a natural gas stream comprising methane is passed to a reforming zone to produce a substrate comprising CO and $H_2$. The substrate is next passed to a bioreactor containing a culture of one or more microorganisms and fermenting the culture to produce one or more fermentation products comprising alcohols and/or acids and an exhaust stream comprising $CO_2$, and $H_2$. The exhaust stream can then be passed to a separation zone to remove at least a portion of the $CO_2$ and produce a purified exhaust stream comprising $H_2$ which is then passed to an ammonia production zone and is used to produce ammonia.

10 Claims, 3 Drawing Sheets

FERMENTATION METHOD

CROSS-REFERENCE TO RELATED APPLICATION

This application claims the benefit of U.S. Provisional Application No. 61/424,893 filed on Dec. 20, 2010 which is incorporated in its entirety by reference.

FIELD OF THE INVENTION

This invention relates to the integration of systems and methods for the production of liquid products into existing industrial processes. The liquid products including alcohol(s) and or acid(s) are produced by microbial fermentation of gas streams comprising CO and optionally $H_2$.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to grow sharply in future, due to an increased interest in ethanol in Europe, Japan, the USA, and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feed stocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major, low cost, energy-rich by-product of the incomplete combustion of organic materials such as coal or oil and oil derived products. For example, the steel industry in Australia is reported to produce and release into the atmosphere over 500,000 tonnes of CO annually. Additionally or alternatively, CO rich gas streams (syngas) can be produced by gasification of carbonaceous materials, such as coal, petroleum and biomass. Carbonaceous materials can be converted into gas products including CO, $CO_2$, $H_2$ and lesser amounts of $CH_4$ by gasification using a variety of methods, including pyrolysis, tar cracking and char gasification. Syngas can also be produced in a steam reformation process, such as the steam reformation of methane or natural gas. Methane can be converted to hydrogen and carbon monoxide and/or carbon dioxide by methane reformation in the presence of a metal catalyst. For example, steam reformation of methane occurs as follows:

$$CH_4 + H_2O \rightarrow CO + 3H_2 \quad (1)$$

$$CO + H_2O \rightarrow CO_2 + H_2 \quad (2)$$

This process accounts for a substantial portion of the hydrogen produced in the world today. Catalytic processes may be used to convert gases consisting primarily of CO and/or CO and hydrogen ($H_2$) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic and acetogenic organisms have been shown to metabolize CO to various end products, namely $CO_2$, $H_2$, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, $CO_2$ and $H_2$ via the acetyl CoA biochemical pathway. For example, various strains of *Clostridium ljungdahlii* that produce ethanol from gases are described in WO 00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is typically associated with co-production of acetate and/or acetic acid. As some of the available carbon is typically converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

WO2007/117157 and WO2008/115080, the disclosure of which are incorporated herein by reference, describe processes that produce alcohols, particularly ethanol, by anaerobic fermentation of gases containing carbon monoxide. Acetate produced as a by-product of the fermentation process described in WO2007/117157 is converted into hydrogen gas and carbon dioxide gas, either or both of which may be used in the anaerobic fermentation process.

The fermentation of gaseous substrates comprising CO, to produce products such as acids and alcohols, typically favours acid production. Alcohol productivity can be enhanced by methods known in the art, such as methods described in WO2007/117157, WO2008/115080, WO2009/022925 and WO2009/064200, which are fully incorporated herein by reference.

U.S. Pat. No. 7,078,201 and WO 02/08438 also describe fermentation processes for producing ethanol by varying conditions (e.g. pH and redox potential) of the liquid nutrient medium in which the fermentation is performed. As disclosed in those publications, similar processes may be used to produce other alcohols, such as butanol.

Microbial fermentation of CO in the presence of $H_2$ can lead to substantially complete carbon transfer into an alcohol. However, in the absence of sufficient $H_2$, some of the CO is converted into alcohol, while a significant portion is converted to $CO_2$ as shown in the following equations:

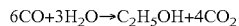

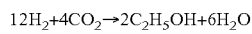

The production of $CO_2$ represents inefficiency in overall carbon capture and if released, also has the potential to contribute to Green House Gas emissions. Furthermore, carbon dioxide and other carbon containing compounds, such as methane, produced during a gasification process may also be released into the atmosphere if they are not consumed in an integrated fermentation reaction.

It is an object of the present invention to provide system(s) and/or method(s) that overcomes disadvantages known in the art and provides the public with new methods for the optimal production of a variety of useful products.

SUMMARY OF THE INVENTION

The present invention provides a method and system which can be integrated into known ammonia production processes with improved efficiencies. Firstly, said integration results in the production of a liquid product such as ethanol. Moreover the integration improves the overall carbon capture efficiency of the ammonia production process by reducing production of $CO_2$. Furthermore the integration of the method and system of the present invention improves the overall energy efficiency of the ammonia production process.

In accordance with a first aspect of the invention, there is provided a method for producing one or more products by microbial fermentation of a waste gas stream used in an ammonia production process, the method comprising;
 a. passing a gas stream comprising natural gas to a conversion zone operated at conditions to convert at least a portion of the gas stream to a substrate comprising CO and $H_2$;
 b. passing at least a portion of the substrate to a bioreactor containing a culture of one or more microorganisms; and
 c. fermenting the culture in the bioreactor to produce one or more fermentation products, said fermentation products comprising alcohols and/or acids.

In particular embodiments the conservation of $H_2$ for production of ammonia is desired, as such in these particular embodiments the anaerobic fermentation of $H_2$ to produce fermentation product is minimal. By way of example, the amount of $H_2$ consumed to produce a fermentation product can be less than 20%, less than 15%, less than 10%, less than 5%, less than 2% or can be 0%.

In some embodiments of the invention, natural gas is converted to a gas stream comprising CO and $H_2$ by means of steam reforming in the presence of a catalyst. Methane remaining in the gas stream after the initial steam reforming stage is then converted to $H_2$ in a secondary reformer.

In some embodiments at least a portion of the gas stream comprising CO and $H_2$ exiting either the steam reformer and/or the secondary reformer is directed to a bioreactor. At least a portion of said gas stream is converted to fermentation products by anaerobic fermentation, said fermentation products comprising alcohol(s) and acid(s). In preferred embodiments the fermentation product is ethanol and/or 2,3-butanediol. In an alternative embodiment the fermentation product is acetate.

In some embodiments, the microbial culture used in the anaerobic fermentation of the fermentation product is a culture of carboxydotrophic bacteria. In various embodiments the carboxydotrophic is selected from *Clostridium, Moorella, Oxobacter, Peptostreptococcus, Acetobacterium, Eubacterium, Butyribacterium* or *Carboxydothermus*. In various embodiments the bacterium is selected from *Clostridium autoethanogenum, Clostridium ljungdahlii, Clostridium acetobutylicm,* or *Clostridium ragsdalei*. In preferred embodiments, the bacterium is *Clostridium autoethanogenum*. In a particular embodiment, the bacterium has the identifying characteristics of accession number DSM10061 or DSM23693 (as filed at the German Collection of Microorganisms and Cell Cultures).

In accordance with some embodiments of the invention, it would be advantageous for the gas stream directed to the bioreactor for the fermentation reaction to be rich in CO. In various embodiments of the present invention the percentage of CO by volume in the gas stream could be at least 40% to 50% CO by volume, from 30% to 40% CO by volume, from 20% to 30% CO by volume, and from 10% to 20% CO by volume. It would be understood by a person skilled in the art that the above ranges of CO content are demonstrative and that the present invention is not limited to gas streams having these concentrations. In some embodiments of the invention it would be suitable to have much lower concentrations of CO in the gas stream, particularly in gas streams where significant amounts of $H_2$ are present.

In another aspect of the present invention, there is provided a system for producing liquid products by microbial fermentation, said system comprising;
 a. a primary reforming means, wherein natural gas is converted to a substrate stream containing CO and $H_2$;
 b. a secondary reforming means, wherein the substrate stream for step 1 is further oxidised in the presence of a catalyst to produce more CO and $H_2$;
 c. a means for directing at least a portion of the substrate stream exiting the primary and/or secondary reforming means to a bioreactor;
 d. said bioreactor being configured to enable the conversion of at least a portion of the CO and/or $H_2$ present in the substrate stream to liquid products by means of microbial fermentation.

A number of processes for reforming natural gas to a substrate stream comprising CO and $H_2$ are known. Examples of reforming processes are provided in WO2009/010347 and are summarised as follows. The principal reforming processes known in the art include steam methane reforming (SMR), auto thermal reforming (ATR), and partial oxidation (POX). Steam methane reforming is a process wherein a methane containing feedstock is reformed in an externally fired reformer in the presence of >2:1 molar steam:methane ratio; auto thermal reforming is a process wherein a methane containing feedstock is reformed in the presence of steam and oxygen; and partial oxidation is a process wherein a methane containing feedstock is reformed in the presence of oxygen and relatively low or zero concentrations of steam.

In some embodiments of the present invention the system may further comprise a means for directing an exhaust gas stream exiting the bioreactor to a known industrial application. For example, in preferred embodiments wherein the bioreactor has been integrated with a known ammonia process, at least a portion of the substrate stream exiting a primary and/or secondary reformer is directed into the bioreactor for the fermentation reaction. The exhaust gas stream exiting the bioreactor is then directed to a $CO_2$ separation zone wherein separation means are used to remove at least a portion of the $CO_2$ from the exhaust gas stream. The resultant $H_2$ rich stream can be used for ammonia production.

In accordance with one specific embodiment of the invention, the bioreactor is integrated into an ammonia production process. In one embodiment, the Water Gas Shift Reactor used in a typical natural gas to ammonia production process is replaced by the bioreactor. The substrate stream exiting the primary or secondary reformers comprising CO, $CO_2$, and $H_2$ is anaerobically fermented in the bioreactor to produce one or more products, and an exhaust gas stream comprising $H_2$ and $CO_2$. The exhaust gas stream is then directed to a $CO_2$ separation zone, and the $CO_2$ is removed, resulting in a $H_2$ rich stream which can be used for ammonia synthesis.

In further embodiments of the invention gases from an ammonia production process ($H_2$, $N_2$ and $CH_4$) can be combined with a stream comprising $CO_2$ to produce acetate. In a particular embodiment the stream comprising $CO_2$ is the tail gas from the bioreactor. In other embodiments the stream comprising $CO_2$ is the $CO_2$ stream removed from the exhaust gas stream in the $CO_2$ separation zone.

In still further embodiments of the invention at least a portion of the ammonia produced can be used to adjust the pH levels in media used in the fermentation process.

In some embodiments of the present invention, the system may comprise a means for determining the composition of the substrate stream, to ensure that the substrate stream has a desirable concentration of CO and/or $H_2$. Said means for determining the composition of the substrate stream may be any known means capable of performing this function.

DETAILED DESCRIPTION OF THE INVENTION

Figure 1:
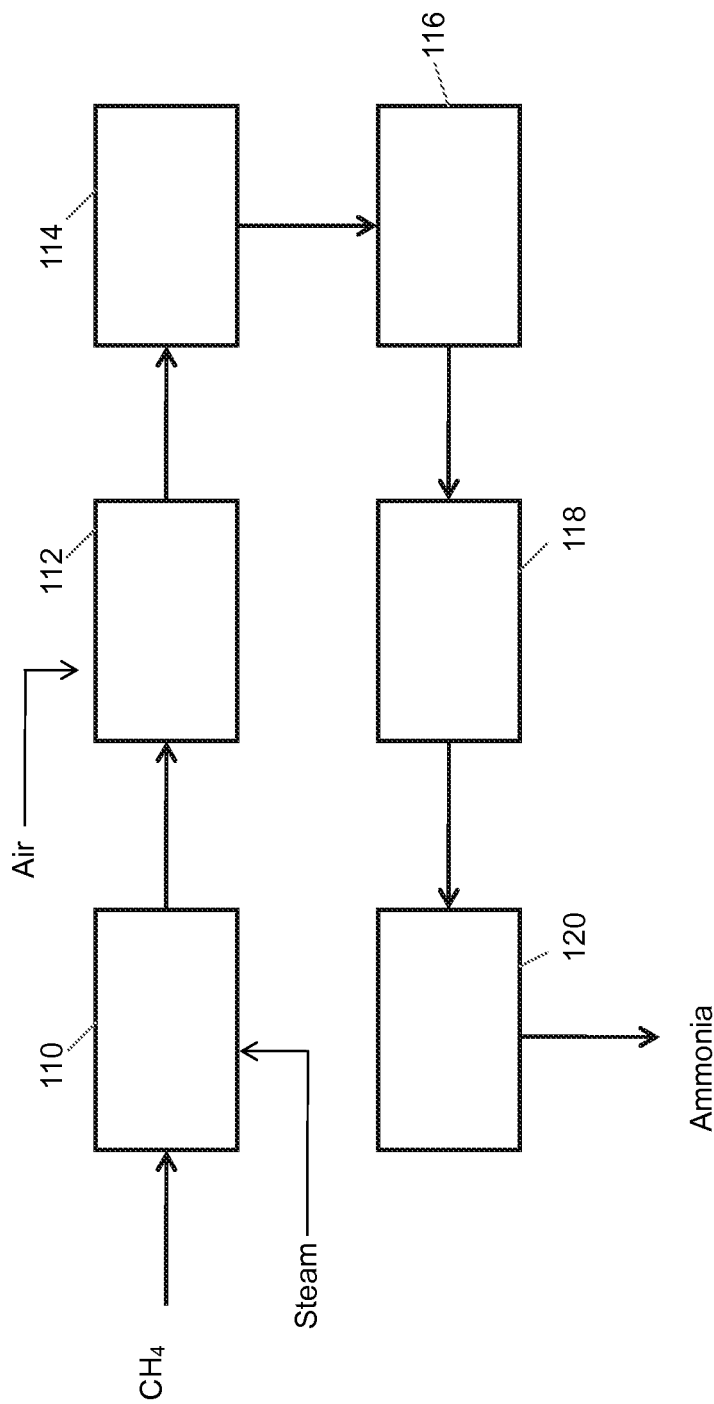
FIG. 1 shows a conventional process for ammonia production.

In accordance with certain aspects of the present invention, a system and method for the fermentation of a substrate stream comprising CO and/or $H_2$ into liquid product, may be integrated into known processes of ammonia production, said integration allowing for the coproduction of desired end products.

In conventional ammonia production a gas is converted into $H_2$ which is then combined with $N_2$ to produce ammonia. It would be understood by a person skilled in the art that said gas may be, but is not limited to, natural gas such as methane or a Liquid Petroleum Gas such as butane or propane.

To describe this process in more detail, firstly a natural gas enters a steam reformer vessel. The natural gas reacts with the steam in the steam reformer to produce a gas stream comprising $H_2$ and CO. The gas stream then enters a secondary reformer in which remaining natural gas is converted into additional $H_2$ and CO as well as $N_2$. The reaction that takes place in the secondary reformer is typically an oxidative reforming step using air as a source of oxygen. The $N_2$ required for the production of ammonia is derived from the reaction that occurs in the secondary reformer. In some known processes, the natural gas may be treated to remove undesirable compounds such as sulfur from the stream, prior to the gas entering the reformer vessel.

In a typical ammonia production process, the gas stream containing $H_2$ and CO then undergoes a water gas shift step in which at least a portion of the CO is reacted with $H_2O$ to produce additional $H_2$ as well as $CO_2$. The gas stream then enters a $CO_2$ absorber in which the $CO_2$ is removed leaving a gas stream containing mostly $H_2$ and $N_2$. The gas stream then enters a methanation step in which any remaining CO is removed. The $H_2$ and $N_2$ rich gas is then ready to be converted to ammonia by way of the ammonia synthesis loop (Haber-Bosch process).

In accordance with the present invention at least a portion of the gas stream containing $H_2$ and CO is directed into a bioreactor instead of into a water gas shift reactor. The integration of a bioreactor into the ammonia production process in conjunction with or instead of a water gas shift reactor provides a number of advantages. For example, the use of a bioreactor to process the gas stream enables the production of fermentation product such as ethanol in addition to the desired end product (ammonia). By directing at least a portion of the syngas stream into the bioreactor, the CO present in the redirected gas stream can be utilised to produce ethanol by a fermentation process. In conventional ammonia production processes this CO would be converted to $CO_2$ by the water gas shift reaction and the resulting $CO_2$ would then be separated from the gas.

In particular embodiments of the present invention, the fermentation reaction taking place in the bioreactor replaces the Water Gas Shift reaction. Replacing the Water Gas Shift Reaction simplifies the ammonia production process. Furthermore replacing the Water Gas Shift Reaction with the fermentation reaction reduces the amount of $CO_2$ in the substrate stream when compared to a typical ammonia production process (reforming→WGS→$CO_2$ removal→methanation→ammonia synthesis) thereby simplifying the $CO_2$ removal step in the ammonia production process.

It has been recognised that at least a portion of the gas stream containing CO and $H_2$ used in earlier stages of the ammonia production process can be converted to ethanol or other liquid products by way of microbial fermentation. A first aspect of the present invention is to provide a method whereby at least a portion of the gas stream comprising $H_2$ and CO is diverted to a bioreactor comprising one or more microorganisms to produce ethanol and/or other liquid products.

In a preferred embodiment of the invention, at least a portion of the gas stream comprising $H_2$ and CO is diverted to the bioreactor instead of passing into a water gas shift reaction vessel. In another embodiment of the invention the entire gas stream is passed into the bioreactor and said bioreactor replaces the water gas shift reaction vessel.

Definitions

Unless stated otherwise, the following terms as used throughout the specification are defined as follows:

The terms "carbon capture" and "overall carbon capture" refer to the efficiency of conversion of a carbon source, such as feedstock, into products. For example the amount of carbon in woody biomass feedstock converted into useful products, such as alcohol.

The term "syngas" refers to a gas mixture that contains at least a portion of carbon monoxide and hydrogen produced by gasification and/or reformation of carbonaceous feedstock.

The term "substrate comprising carbon monoxide" and like terms should be understood to include any substrate in which carbon monoxide is available to one or more strains of bacteria for growth and/or fermentation.

"Gaseous substrates comprising carbon monoxide" include any gas which contains carbon monoxide. The gaseous substrate will typically contain a significant proportion of CO, preferably at least about 5% to about 95% CO by volume.

The term "bioreactor" includes a fermentation device consisting of one or more vessels and/or towers or piping arrangements, which includes the continuous stirred tank reactor (CSTR), an immobilised cell reactor, a gas-lift reactor, a bubble column reactor (BPR), a membrane reactor, such as Hollow Fibre Membrane Bioreactor (HFMBR) or a trickle bed reactor (TBR), or other vessel or other device suitable for gas-liquid contact.

The term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. In addition, the term "acetate" includes both acetate salt alone and a mixture of molecular or free acetic acid and acetate salt, such as the mixture of acetate salt and free acetic acid present in a fermentation broth as described herein.

The term "desired composition" is used to refer to the desired level and types of components in a substance, such as, for example, of a gas stream. More particularly, a gas is considered to have a "desired composition" if it contains a particular component (e.g. CO and/or $H_2$) and/or contains a particular component at a particular level and/or does not contain a particular component (e.g. a contaminant harmful to the microorganisms) and/or does not contain a particular component at a particular level. More than one component may be considered when determining whether a gas stream has a desired composition.

The term "stream" is used to refer to a flow of material into, through and away from one or more stages of a process, for example, the material that is fed to a bioreactor and/or an optional $CO_2$ remover. The composition of the stream may vary as it passes through particular stages. For example, as a stream passes through the bioreactor, the CO content of the stream may decrease, while the $CO_2$ content may increase. Similarly, as the stream passes though the $CO_2$ remover stage, the $CO_2$ content will decrease.

Unless the context requires otherwise, the phrases "fermenting", "fermentation process" or "fermentation reaction" and the like, as used herein, are intended to encompass both the growth phase and product biomass of the process.

The terms "increasing the efficiency", "increased efficiency" and the like, when used in relation to the fermentation process, include, but are not limited to, increasing one or more of: the rate of growth of micro-organisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of the fermentation, and further may reflect the value (which may be positive or negative) of any by-products generated during the process.

Conventional ammonia production typically involves a reforming step in which a natural gas comprising methane ($CH_4$) is converted to CO and $H_2$. The reforming step occurs in a reforming zone in the presence of a metal catalyst and at elevated temperatures. A common reforming process is steam reforming, in which the methane reacts with steam in the presence of a metal catalyst at an elevated temperature. The metal catalyst commonly used for steam reforming is a nickel catalyst, and the reaction commonly occurs at temperatures between 700-1100° C. The stoichiometry of the conversion is as follows:

$$CH_4 + H_2O \xrightleftharpoons[Ni/800°C.]{} CO + 3H_2$$

The syngas stream exiting the steam reformer typically comprises $H_2$, CO, $CO_2$ and $CH_4$.

The syngas stream is then directed into a secondary reformer. Air is introduced to the secondary reformer as an oxygen source, which enables the provision of $N_2$ required for ammonia production. Additionally in this step excess $CH_4$ in the syngas is converted to CO and $H_2$ using the same reaction described above.

The syngas stream exiting the secondary reformer ideally comprises $H_2$, CO, $CO_2$, $N_2$ and small amounts of $CH_4$. In conventional ammonia production the gas stream is then directed into a Water Gas Shift reactor.

The reactions occurring in the primary steam reformer and the secondary reformer are endothermic in nature. The levels of CO, $CO_2$ and $H_2$ produced by the reformers can be affected by a number of factors including the levels of $O_2$, amount of Steam provided to the reformers and the amount of methane provided. Other factors which may influence the production levels of CO, $CO_2$ and $H_2$ include the temperature and pressure levels in the reformers when the reaction occurs.

In other embodiments of the present invention, a natural gas can be oxidised by alternative methods to steam reforming. Another method of oxidising a natural gas to CO and $H_2$ is auto thermal reforming. In auto thermal reforming a natural gas such as methane is partially oxidised in the presence of oxygen at elevated temperature and pressure as follows:

$$2CH_4 + O_2 + CO_2 \rightarrow 3H_2 + 3CO + H_2O$$

$$2CH_4 + O_2 + H_2O \rightarrow 5H_2 + 2CO$$

Another alternative to the steam reforming process is dry reforming of $CO_2$ which takes advantage of the significant portion of $CO_2$ present in biogas or other sources of natural gas to produce carbon monoxide and hydrogen as follows:

$$CH_4 + CO_2 \rightarrow 2CO + 2H_2$$

In a first embodiment of the present invention at least a portion of the syngas exiting the primary steam reformer is directed to a bioreactor for conversion to liquid products by microbial fermentation.

In a second embodiment of the present invention at least a portion of the syngas exiting the secondary reformer is directed to a bioreactor for conversion to liquid products by microbial fermentation.

In said first and second embodiments of the present invention, the exhaust gas stream exiting the bioreactor is rich in $H_2$ and $N_2$ and additionally comprises CO, $CO_2$, $CH_4$. Said exhaust gas stream is then passed to a separation zone comprising a $CO_2$ absorber.

In said first and second embodiments of the present invention, a portion of the syngas not directed to the bioreactor is passed through the water gas shift reactor. The syngas in the water gas shift reactor undergoes a water gas shift reaction wherein CO and $H_2O$ are converted into $CO_2$ and $H_2$ according to the following stoichiometry:

$$CO + H_2O \xrightleftharpoons[Ni/800°C.]{} CO_2 + H_2$$

According to said first and second embodiments of the invention, the exhaust gas exiting the bioreactor and the tail gas exiting the water gas shift reaction vessel are then directed to a separation zone comprising a $CO_2$ absorber used in conventional ammonia production. In a third embodiment of the invention all of the syngas exiting the secondary reformer is directed to a bioreactor for conversion to liquid products by microbial fermentation. In said third embodiment the bioreactor replaces the water gas shift reaction vessel. In the above embodiments, the tail gas exiting the bioreactor and/or water gas shift reactor proceeds through conventional steps for ammonia production, said steps include being passed through a $CO_2$ separation zone wherein $CO_2$ is removed. The tail gas from this process is then passed through a methanation step wherein any remaining CO is removed from the gas stream. The remaining gas is very rich in $H_2$ and $N_2$ and may contain trace amounts of $CH_4$. The gas is then passed into an ammonia synthesis zone, wherein ammonia is produced.

The $CO_2$ can be removed from the tail gas by known methods. A number of methods can be used for removing $CO_2$ from a gas stream including pressure swing adsorption (PSA), adsorption using solvents and cryogenic fractionation. Other methods of $CO_2$ separation that may be used include extraction with a metal oxide, such as CaO, and use of porous carbon or selective solvent extraction such as amine extraction. Amines such as aqueous monoethanolamine (MEA), diglycolamine (DGA), diethanolamine (DEA), diisopropanolamine (DIPA) and methyldiethanolamine (MDEA) are widely used industrially for removing $CO_2$ and hydrogen sulfide from natural gas streams and refinery process streams.

In some embodiments of the invention, the fermentation reaction taking place in the bioreactor may consume CO in the gas stream whilst preserving $H_2$. The preservation of $H_2$ in the gas stream, resulting in a gas stream rich in $H_2$ exiting the bioreactor is advantageous, as it allows for optimal coproduction of ammonia. The fermentation reaction is described in further detail below.

Figure 2:
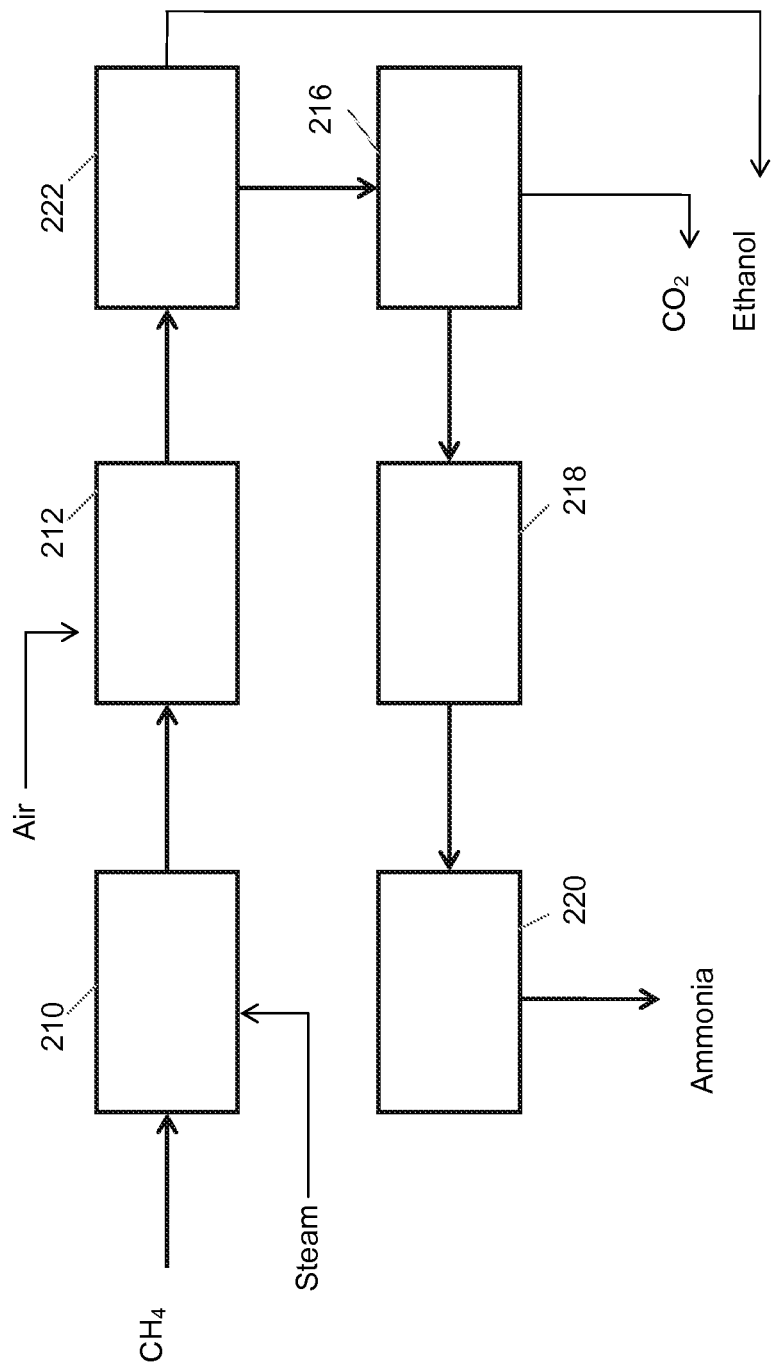
FIG. 2 shows an embodiment of the present invention wherein all of a gas stream exiting a secondary reformer is directed into a bioreactor for fermentation of CO and/or $H_2$ into liquid product(s).

Referring to FIG. 2, a particular embodiment of the present invention is presented. Natural gas (methane) is directed into a steam reformer in the presence of steam. The methane and steam react to produce a syngas containing CO, $CO_2$ and $H_2$. The syngas is then directed into a secondary reformer. Air is also introduced to the secondary reformer, and the $O_2$ in the air reacts with additional methane in the gas stream to produce more $H_2$. The introduction of air in this stage introduces the $N_2$ required by the process to produce ammonia. The gas stream exiting the secondary reformer which contains $H_2$, CO, $CO_2$ and $N_2$, is directed into a bioreactor. The bioreactor in this embodiment of the present invention replaces the WGS reactor used in conventional ammonia production processes. The fermentation reaction in the bioreactor converts CO and optionally $H_2$ to ethanol by way of anaerobic fermentation. It is desirable for the conversion of $H_2$ to be minimal, as higher levels of $H_2$ in the exhaust gas stream leaving the bioreactor will result in a higher yield of ammonia. The gas stream is then directed into a $CO_2$ separation zone wherein the $CO_2$ is separated from the gas stream and provides a purified exhaust gas stream. The purified gas stream, rich in $H_2$ and $N_2$ is then directed to a methanation zone, wherein any remaining CO in the purified gas stream is removed to produce an ammonia synthesis feed stream. The ammonia synthesis feed stream is then directed into an ammonia synthesis zone for ammonia production.

The separated $CO_2$ can be utilised in a urea production plant. Alternatively, in ammonia processing plants which are not linked to a urea plant, it may be possible to recycle the separated $CO_2$ back into the steam reformer and the secondary reformer. Another possible use for the separated $CO_2$ is the production of acetate (how, fermentation) using at least a part of the $H_2/N_2$ gas stream.

Figure 3:
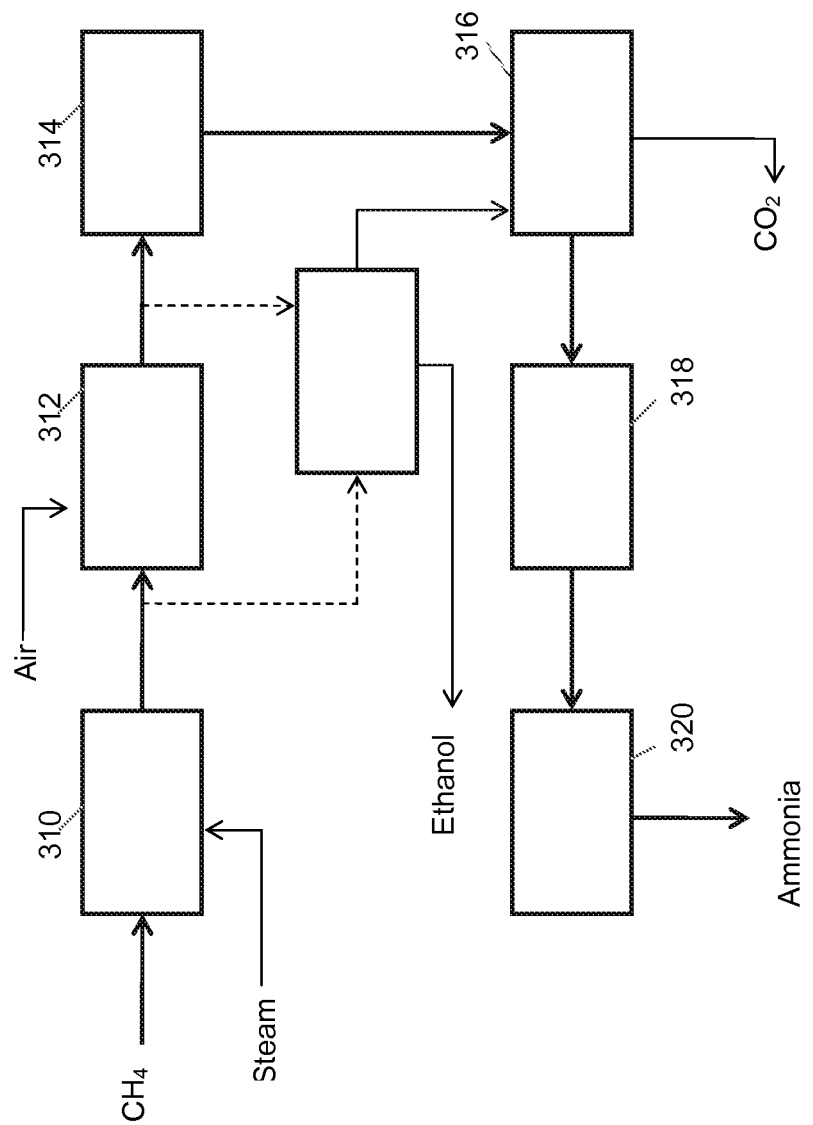
FIG. 3 shows another embodiment of the invention, wherein at least a portion of a gas stream comprising CO and $H_2$ is directed into a bioreactor for fermentation of CO and/or $H_2$ into liquid product(s).

FIG. 3 demonstrates another embodiment of the present invention wherein at least a portion of the gas stream leaving the steam reformer and/or the secondary reformer is directed into the bioreactor for the production of ethanol. Unlike FIG. 2, the bioreactor in this embodiment does not replace the WGS reactor.

In a particular aspect of the above embodiments the liquid products produced by microbial fermentation in the bioreactor include acid(s) and/or alcohol(s). In a particular embodiment, the product is ethanol. The coproduction of ammonia and ethanol would be attractive for the production of ethylamines by a reaction as follows:

$$CH_3CH_2OH + NH_3 \rightarrow CH_3CH_2NH_2 + H_2O$$

Ethylamines are useful in chemical industry as industrial solvents. As previously noted, ethylamines can be used for solvent systems for removal of $H_2S$ and/or $CO_2$ from industrial gas streams. Ethylamines can also be used in the production of herbicides.

It would be understood by a person skilled in the art that the acid(s) and/or alcohol(s) produced by the anaerobic fermentation reaction are not limited to that of acetate and ethanol. Further examples of products derived from the fermentation reaction include but are not limited to acetate, butyrate, propionate, caproate, ethanol, propanol, butanol and hydrogen. By way of example, these products may be produced by fermentation using microns from the genus *Moorella, Clostridia, Ruminococcus, Acetobacterium, Eubacterium, Butyribacterium, Oxobacter, Methanosarcina* and *Desulfotomaculum*.

Ammonia Production

Referring to FIG. 1, a common method of ammonia production involves the following steps;
  a. treating natural gas to remove $H_2S$,
  b. production of syngas (CO and $H_2$),
  c. purification of syngas (removal of $CO_2$), and
  d. synthesis of ammonia.

The first step is to remove sulphur compounds from the feedstock, as sulphur deactivates the catalysts used later in the process. Sulfur can be removed by catalytic hydrogenation to convert sulphur compounds in the feedstock to gaseous hydrogen sulphide as follows;

$$H_2 + RSH \rightarrow RH + H_2S(gas)$$

The gaseous hydrogen sulphide is then absorbed and removed by passing it through beds of zinc oxide where it is converted to solid zinc sulphide:

$$H_2S + ZnO \rightarrow ZnS + H_2O$$

The second step involves three reactions. The first is the conversion of methane to CO, $CO_2$ and $H_2$ (syngas) at high temperatures (770° C.) in the presence of a nickel catalyst in a steam reformer 110. The stoichiometry of the conversion is as follows;

$$CH_4 + H_2O \rightleftharpoons 3H_2 + CO$$

$$CH_4 + 2H_2O \rightleftharpoons 4H_2 + CO_2$$

$$CO + H_2O \leftrightharpoons H_2 + CO_2$$

Next the syngas is cooled slightly and directed into a secondary reformer 112. The reactions are:

$$CO + H_2O \leftrightharpoons CO_2 + H_2$$

$$O_2 + 2CH_4 \leftrightharpoons 2CO + 4H_2$$

$$O_2 + CH_4 \leftrightharpoons 2CO_2 + 2H_2$$

$$2O_2 + CH_4 \leftrightharpoons 2H_2O + CO_2$$

The addition of air to the secondary reformer introduces nitrogen which is required for ammonia synthesis.

The next reaction is the removal of CO. The CO is converted to $CO_2$ in a water gas shift reactor 114 as follows:

$$CO + H_2O \leftrightharpoons CO_2 + H_2$$

The water gas shift reaction takes place over two stages. Initially the gas stream is passed over a $Cr/Fe_3O_4$ catalyst at 360° C., and then the gas is passed over a Cu/ZnO/Cr catalyst at 210° C. The use of a two stage reaction maximises the conversion of CO to $CO_2$.

The next step of the ammonia production process is the removal of $CO_2$ in a $CO_2$ separation zone 116. As previously discussed there are a number of different methods for removing $CO_2$ from a gas stream including pressure swing adsorption (PSA), adsorption using solvents and cryogenic fractionation and solvent extraction.

A methanation step is used to remove the remaining CO from the gas stream.

$$CO + 3H_2 \rightarrow CH_4 + H_2O$$

This is a catalytic reaction taking place between 400-600° C.

The resulting gas stream contains $H_2$ and $N_2$ and the synthesis of ammonia can now take place. The gas is cooled, compressed and fed into the ammonia synthesis loop. The reaction between $N_2$ and $H_2$ to produce ammonia gas is an exothermic equilibrium reaction which releases 92.4 KJ/mol of energy at 298K.

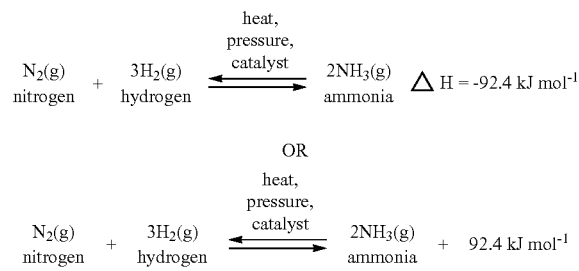

By using a pressure of around 200 atm and a temperature of about 500° C., it is possible to produce ammonia yields of around 10-20%. The remaining mixture of gases is recycled through the reactor, and the heat released by the reaction is used to heat the incoming gas mixture.

Fermentation Reaction

Particular embodiments of the invention include the fermentation of a syngas substrate stream to produce products including alcohol(s) and optionally acid(s). Processes for the production of ethanol and other alcohols from gaseous substrates are known. Exemplary processes include those described for example in WO2007/117157, WO2008/115080, U.S. Pat. No. 6,340,581, U.S. Pat. No. 6,136,577, U.S. Pat. No. 5,593,886, U.S. Pat. No. 5,807,722 and U.S. Pat. No. 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus *Clostridium*, such as strains of *Clostridium ljungdahlii*, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091) and *Clostridium autoethanogenum* (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Morella thermoacetica*, *Moorella thermoautotrophica*, *Ruminococcus productus*, *Acetobacterium woodii*, *Eubacterium limosum*, *Butyribacterium methylotrophicum*, *Oxobacter pfennigii*, *Methanosarcina barkeri*, *Methanosarcina acetivorans*, *Desulfotomaculum kuznetsovii* (Simpa et. al. Critical Reviews in Biotechnology, 2006 Vol. 26. pp 41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In another embodiment, the *Clostridium autoethanogenum* is a *Clostridium autoethanogenum* having the identifying characteristics of DSMZ deposit number DSMZ 10061. In another embodiment, the *Clostridium autoethanogenum* is a *Clostridium autoethanogenum* having the identifying characteristics of DSMZ deposit number DSMZ 23693. Examples of fermentation of a substrate comprising CO to produce products including alcohols by *Clostridium autoethanogenum* are provided in WO2007/117157, WO2008/115080, WO2009/022925, WO2009/058028, WO2009/064200, WO2009/064201, WO2009/113878 and WO2009/151342 all of which are incorporated herein by reference.

Culturing of the bacteria used in the methods of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (vi) J.

L. Vega, et al. (1989). Study of gaseous substrate fermentations: Carbon monoxide conversion to acetate. 1. Batch culture. Biotechnology and Bioengineering. 34. 6. 774-784; (vii) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactor configured for gas/liquid contact wherein the substrate can be contacted with one or more microorganisms, such as a continuous stirred tank reactor (CSTR), an immobilised cell reactor, a gas-lift reactor, a bubble column reactor (BCR), a membrane reactor, such as a Hollow Fibre Membrane Bioreactor (HFMBR) or a trickle bed reactor (TBR), monolith bioreactor or loop reactors. Also, in some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

According to various embodiments of the invention, the carbon source for the fermentation reaction is syngas derived from gasification. The syngas substrate will typically contain a major proportion of CO, such as at least about 15% to about 75% CO by volume, from 20% to 70% CO by volume, from 20% to 65% CO by volume, from 20% to 60% CO by volume, and from 20% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when $H_2$ and $CO_2$ are also present. In particular embodiments, the presence of hydrogen results in an improved overall efficiency of alcohol production. The gaseous substrate may also contain some $CO_2$ for example, such as about 1% to about 80% $CO_2$ by volume, or 1% to about 30% $CO_2$ by volume.

In accordance with particular embodiments of the invention, the CO content and/or the $H_2$ content of the reformed substrate stream can be enriched prior to passing the stream to the bioreactor. For example, hydrogen can be enriched using technologies well known in the art, such as pressure swing adsorption, cryogenic separation and membrane separation. Similarly, CO can be enriched using technologies well known in the art, such as copper-ammonium scrubbing, cryogenic separation, COSORB™ technology (absorption into cuprous aluminium dichloride in toluene), vacuum swing adsorption and membrane separation. Other methods used in gas separation and enrichment are detailed in PCT/NZ2008/000275, which is fully incorporated herein by reference.

Typically, the carbon monoxide will be added to the fermentation reaction in a gaseous state. However, the methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a micro bubble dispersion generator (Hensirisak et. al. Scale-up of micro bubble dispersion generator for aerobic fermentation; *Applied Biochemistry and Biotechnology Volume* 101, *Number* 3/*October,* 2002) could be used for this purpose.

It will be appreciated that for growth of the bacteria and CO-to-alcohol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/117157, WO2008/115080, WO2009/022925, WO2009/058028, WO2009/064200, WO2009/064201, WO2009/113878 and WO2009/151342 referred to above. The present invention provides a novel media which has increased efficacy in supporting growth of the micro-organisms and/or alcohol production in the fermentation process. This media will be described in more detail hereinafter.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO2007/117157, WO2008/115080, WO2009/022925, WO2009/058028, WO2009/064200, WO2009/064201, WO2009/113878 and WO2009/151342 all of which are incorporated herein by reference.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per liter per day.

It is also desirable that the rate of introduction of the CO and $H_2$ containing gaseous substrate is such as to ensure that the concentration of CO in the liquid phase does not become limiting. This is because a consequence of CO-limited conditions may be that the ethanol product is consumed by the culture.

Product Recovery

The products of the fermentation reaction can be recovered using known methods. Exemplary methods include those described in WO2007/117157, WO2008/115080, WO2009/022925, U.S. Pat. No. 6,340,581, U.S. Pat. No. 6,136,577, U.S. Pat. No. 5,593,886, U.S. Pat. No. 5,807,722 and U.S. Pat. No. 5,821,111. However, briefly and by way of example only ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit. Most of the ethanol is vaporized and condensed while the oleyl alcohol is non volatile and is recovered for re-use in the fermentation.

Acetate, which is produced as by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol- and acetate-containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and co-solvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

General

Embodiments of the invention are described by way of example. However, it should be appreciated that particular steps or stages necessary in one embodiment may not be necessary in another. Conversely, steps or stages included in the description of a particular embodiment can be optionally advantageously utilised in embodiments where they are not specifically mentioned.

While the invention is broadly described with reference to any type of stream that may be moved through or around the system(s) by any known transfer means, in certain embodiments, the biogas and reformed and/or blended substrate streams are gaseous. Those skilled in the art will appreciate that particular stages may be coupled by suitable conduit means or the like, configurable to receive or pass streams throughout a system. A pump or compressor may be provided to facilitate delivery of the streams to particular stages. Furthermore, a compressor can be used to increase the pressure of gas provided to one or more stages, for example the bioreactor. As discussed hereinabove, the pressure of gases within a bioreactor can affect the efficiency of the fermentation reaction performed therein. Thus, the pressure can be adjusted to improve the efficiency of the fermentation. Suitable pressures for common reactions are known in the art.

In addition, the systems or processes of the invention may optionally include means for regulating and/or controlling other parameters to improve overall efficiency of the process. For example particular embodiments may include determining means to monitor the composition of substrate and/or exhaust stream(s). In addition, particular embodiments may include a means for controlling the delivery of substrate stream(s) to particular stages or elements within a particular system if the determining means determines the stream has a composition suitable for a particular stage. For example, in instances where a gaseous substrate stream contains low levels of CO or high levels of $O_2$ that may be detrimental to a fermentation reaction, the substrate stream may be diverted away from the bioreactor. In particular embodiments of the invention, the system includes means for monitoring and controlling the destination of a substrate stream and/or the flow rate, such that a stream with a desired or suitable composition can be delivered to a particular stage.

In addition, it may be necessary to heat or cool particular system components or substrate stream(s) prior to or during one or more stages in the process. In such instances, known heating or cooling means may be used.

Various embodiments of the systems of the invention are described in the accompanying Figures.

As shown in FIG. 2, one embodiment of the invention provides a system and method for the production of one or more products, from a gas stream used in an ammonia production process, wherein a bioreactor replaces the water gas shift reactor, found in typical ammonia production systems. In accordance with FIG. 2 a natural gas stream is provided to a steam reformer 210 wherein the natural gas stream is reacted to produce a reformed stream comprising $H_2$, CO and $CO_2$, and unreacted $CH_4$. The reformed stream is then directed to a secondary reformer 212, wherein the reformed stream is reacted to produce a substrate stream comprising $H_2$, CO, $CO_2$, $N_2$ and traces of $CH_4$. The substrate stream is passed to a bioreactor 222. The substrate stream is fermented in the bioreactor by a culture comprising one or more anaerobic microorganisms to produce one or more fermentation products, and an exhaust gas stream comprising $H_2$, $CO_2$, $N_2$ and small or trace amounts of $CH_4$ and CO. The exhaust gas stream is passed to a $CO_2$ separation zone 216, wherein $CO_2$ is separated from the exhaust gas stream, resulting in a hydrogen rich gas stream, and a $CO_2$ gas stream. The $CO_2$ gas stream can then be directed to a urea plant. The hydrogen rich gas stream is directed to a methanation vessel 218 wherein any remaining CO present in the stream is removed. The resulting hydrogen rich gas stream is then passed to an ammonia synthesis zone 220 for the production of ammonia.

FIG. 3 depicts an alternative method and system of the invention, wherein the bioreactor is provided as well as a water gas shift reactor. In FIG. 3 a natural gas stream is provided to a steam reformer 310 wherein the natural gas stream is reacted to produce a reformed stream comprising $H_2$, CO and $CO_2$, and $CH_4$. At least a portion of the reformed stream is then directed to a secondary reformer 312, wherein the reformed stream is reacted to produce a substrate stream comprising $H_2$, CO, $CO_2$, $N_2$ and traces of $CH_4$, which is then passed to a Water Gas Shift Reactor (WGSR) 314, wherein the CO present in the stream is reacted with $H_2O$ to produce $CO_2$. As shown in FIG. 3, a portion of either or both of the streams exiting the steam reformer 310 and/or the secondary reformer 312 can be directed to a bioreactor 322 instead of the WGSR 314. The bioreactor functions to remove CO from the stream, and produces one or more fermentation products. The exhaust gas stream exiting the bioreactor 322 is directed to the $CO_2$ separation zone 316 along with the gas stream exiting the WGSR 314. The $CO_2$ absorber separates $CO_2$ from the gas stream resulting in a hydrogen rich gas stream. The hydrogen rich gas stream is treated in a methanation vessel 318 to remove any traces of CO in the gas, before being passed into an ammonia synthesis zone for the production of ammonia.

The invention has been described herein with reference to certain preferred embodiments, in order to enable the reader to practice the invention without undue experimentation. Those skilled in the art will appreciate that the invention can be practiced in a large number of variations and modifications other than those specifically described. It is to be understood that the invention includes all such variations and modifications. Furthermore, titles, heading, or the like are provided to aid the reader's comprehension of this document, and should not be read as limiting the scope of the present invention. The entire disclosures of all applications, patents and publications cited herein are herein incorporated by reference.

More particularly, as will be appreciated by one of skill in the art, implementations of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps, and/or systems and/or methods omitting one or more steps.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

EXAMPLES

Media Preparation

| Solution A | | | |
|---|---|---|---|
| $NH_4Ac$ | 3.083 g | KCl | 0.15 g |
| $MgCl_2 \cdot 6H_2O$ | 0.61 g | NaCl | 0.12 g |
| $CaCl_2 \cdot 2H_2O$ | 0.294 g | Distilled Water | Up to 1 L |
| Solution B | | | |
| Component/ 0.1M solution (aq) | Component/ 0.1M solution (aq) | Component/ 0.1M solution (aq) | Component/ 0.1M solution (aq) |
| Component/ 0.1M solution (aq) | Quantity/ml into 1 L media | Component/ 0.1M solution (aq) | Quantity/ml into 1 L media |
| $FeCl_3$ | 1 ml | $Na_2WO_4$ | 0.1 ml |
| $CoCl_2$ | 0.5 ml | $ZnCl_2$ | 0.1 ml |
| $NiCl_2$ | 0.5 ml | $Na_2MoO_4$ | 0.1 ml |
| $H_3BO_3$ | 0.1 ml | | |
| Solution C | | | |
| Biotin | 20.0 mg | Calcium D-(*)-pantothenate | 50.0 mg |
| Folic acid | 20.0 mg | Vitamin B12 | 50.0 mg |
| Pyridoxine. HCl | 10.0 mg | p-Aminobenzoic acid | 50.0 mg |
| Thiamine. HCl | 50.0 mg | Thioctic acid | 50.0 mg |
| Riboflavin | 50.0 mg | Distilled water | To 1 Litre |
| Nicotinic acid | 50.0 mg | | |

1.4 liters of media solution A was aseptically and anaerobically transferred into a 2 L CSTR vessel, and continuously sparged with $N_2$. Once transferred to the fermentation vessel, the reduction state and pH of the transferred media could be measured directly via probes. The media was heated to 37° C. and stirred at 400 rpm and 1.5 ml of resazurin (2 g/L) was added. 1.0 ml of $H_3PO_4$ 85% was added to obtain a 10 mM solution. The pH was adjusted to 5.3 using $NH_4OH$. Metal ions were added according to solution B and 15 ml of solution C was added. 3 mmol cysteine-HCl was added and the pH was adjusted to pH 5.5 using $NH_4OH$.

Bacteria: *Clostridium autoethanogenum* was obtained from the German Resource Centre for Biological Material (DSMZ) under the identifying deposit number DSM23693.

Gaseous Substrate: The biogas source for the gaseous substrate for this experiment was derived from methane. The methane was converted to gaseous substrate comprising CO by a steam reforming process. The steam reforming was carried out in an Inconel® 800 reactor at a temperature of around 818° C. and a temperature of around 128 psig. The reactor was loaded with a nickel-alumina catalyst and a steam to carbon ration (S/C) of 3.6 was used for the biogas reforming. Prior to the reforming process, the methane was blended with $CO_2$ to obtain a $CH_4/CO_2$ ratio of about 1.5. Steam reforming of the methane resulted in a gaseous substrate having the following composition; $H_2$ 64.7%, $N_2$ 7.69%, CO 14.1%, $CO_2$ 8.8%, $H_2S$ 0.0%.

Fermentation in serumbottle: Incubation was performed in two 250 ml sealed serum bottles (SB1, SB2) containing 50 ml of media. Each bottle was inoculated with 1 ml of a growing culture of *Clostridium autoethanogenum* (DSM23693). The headspace gas was then evacuated and filled to an overpressure of 25 psig with the steam reformed methane gas comprising CO. A shaking incubator was used and the reaction temperature was maintained at 37° C.

Sampling and analytical procedures: Media samples were taken from the serum bottles at intervals over periods up to 44 hours. Each time the media was sampled care was taken to ensure that no gas was allowed to enter into or escape from the serum bottle. HPLC was routinely used to quantify the level of acetate and ethanol during the fermentation.

HPLC: HPLC System Agilent 1100 Series. Mobile Phase: 0.0025N Sulfuric Acid. Flow and pressure: 0.800 mL/min. Column: Alltech IOA; Catalog #9648, 150×6.5 mm, particle size 5 µm. Temperature of column: 60° C. Detector: Refractive Index. Temperature of detector: 45° C.

Method for sample preparation: 400 µL of sample and 50 µL of 0.15M $ZnSO_4$ are mixed and loaded into an Eppendorf tube. The tubes are centrifuged for 3 min. at 12,000 rpm, 4° C. 200 µL of the supernatant are transferred into an HPLC vial, and 5 µL are injected into the HPLC instrument.

Pressure measurements: Head space pressure measurements were taken from the serumbottles at intervals over periods up to 3 days. After the reaction had finished the final headspace composition was analysed by Gas Chromatography.

Gas Chromatography: Gas Chromatograph HP 5890 series II utilizing a Flame Ionization Detector. Capillary GC Column: EC1000—Alltech EC1000 30 m×0.25 mm×0.25 µm. The Gas Chromatograph was operated in Split mode with a total flow of hydrogen of 50 mL/min with 5 mL purge flow (1:10 split), a column head pressure of 10 PSI resulting in a linear velocity of 45 cm/sec. The temperature program was initiated at 60° C., held for 1 minute then ramped to 215° C. at 30° C. per minute, then held for 2 minutes. Injector temperature was 210° C. and the detector temperature was 225° C.

Results

TABLE 1

| Serum bottle | Date | incubation time (days) | Acetate (g/L) | Ethanol (g/L) | Headspace (PSI) |
|---|---|---|---|---|---|
| SB1 | Aug. 6, 2011 13:45 | 0.0 | 0.88 | 0.09 | 24.0 |
| SB2 | Aug. 6, 2011 13:46 | 0.0 | 0.9 | 0.12 | 24.6 |
| SB1 | Sep. 6, 2011 12:33 | 1.0 | 1.44 | 0.19 | 22.8 |
| SB2 | Sep. 6, 2011 12:33 | 1.0 | 1.57 | 0.17 | 21.3 |
| SB1 | Oct. 6, 2011 9:25 | 1.8 | 1.39 | 0.44 | 17.9 |
| SB2 | Oct. 6, 2011 9:25 | 1.8 | 1.49 | 0.45 | 19.2 |

TABLE 2

| | | Gas Composition | | | | |
|---|---|---|---|---|---|---|
| Serumbottle | Incubation Time | $CO_2$ | CO | $H_2$ | $N_2$ | $H_2S$ (ppm) |
| Start composition | 0.0 | 8.8% | 14.1% | 64.7 | 7.7% | 0 |
| SB1 | 1.8 | 15.7% | 0.0% | 75.6% | 7.4% | 13400 |
| SB2 | 1.8 | 15.6% | 0.0% | 75.7% | 7.2% | 13190 |

Table 1 shows the HPLC and headspace pressure for the two serum bottles over the duration of the fermentation. The metabolites measurements were determined immediately after inoculation and after 1.0 and 1.8 days incubation. Table 2 shows the initial gas composition in the headspace at day 0.0 and the final headspace composition at day 1.8. The results clearly show utilisation of CO. SB2 shows a decrease in CO % from 14.1% to 0.0% and an increase in $CO_2$ from 8.8% to 15.7%. Correspondingly both serum bottles show an increase in the metabolite levels between day 0.0 and day 2.9. The above results demonstrate the fermentation of CO by *C. autoethanogenum* to produce ethanol and acetate. The Hydrogen values fluctuate due to inefficient GC calibration at high $H_2$ levels but don't influence the carbon balance.

What I claim is:

1. An integrated ammonia production and fermentation method for producing one or more products from a gas stream comprising methane, the method comprising;
   a) converting at least a portion of a gas stream comprising methane to a substrate comprising CO, $CO_2$ and $H_2$;
   b) passing at least a portion of the substrate to a bioreactor containing a culture of one or more carboxydotrophic bacteria, anaerobically fermenting at least a first portion of the substrate comprising CO and $H_2$ to produce one or more products comprising alcohols and/or acids and an exhaust gas stream comprising hydrogen and carbon dioxide;
   c) passing a second portion of the substrate to a water gas shift reactor operated at conditions to produce an effluent stream comprising $CO_2$ and $H_2$;
   d) passing the exhaust gas stream and the effluent stream of (c) to a separation zone operated at conditions to separate at least a portion of the $CO_2$ and produce a second effluent stream rich in $H_2$ and a $CO_2$ stream; and
   e) passing the second effluent stream to an ammonia synthesis zone operated at conditions to produce ammonia.

2. The method of claim 1 wherein the gas stream is converted to a substrate stream comprising CO, $CO_2$ and $H_2$ by a steam reforming process.

3. The method of claim 2 wherein the substrate stream is passed into a secondary reformer, wherein at least a portion of methane remaining in the substrate stream is converted to CO, $CO_2$ and $H_2$, prior to being passed to the bioreactor.

4. The method of claim 1 wherein the one or more products is selected from the group consisting of ethanol; 2,3-butanediol, and acetic acid.

5. The method of claim 1 wherein prior to passing the effluent stream to the ammonia synthesis zone, it is passed to a methanation zone to remove traces of CO.

6. The method according to claim 1 wherein the carboxydotrophic bacterium is selected from the group comprising *Moorella*, *Clostridium*, *Ruminococcus*, *Acetobacterium*, *Eubacterium*, *Butyribacterium*, *Oxobacter*, *Methanosarcina*, *Methanosarcina*, and *Desulfotomaculum*.

7. The method of claim 6 wherein the carboxydotrophic bacterium is *Clostridium autoethanogenum*.

8. An integrated ammonia production and fermentation method for producing one or more products from a gas stream comprising methane, the method comprising;
   a) converting at least a portion of a gas stream comprising methane to a substrate comprising CO, $CO_2$ and $H_2$;
   b) passing the substrate to a bioreactor containing a culture of one or more carboxydotrophic bacteria, anaerobically fermenting at least a portion of the substrate to produce one or more products comprising alcohols and/or acids and an exhaust gas stream comprising hydrogen and carbon dioxide;
   c) passing the exhaust gas stream to a separation zone operated at conditions to separate at least a portion of the $CO_2$ and produce a second effluent stream rich in $H_2$ and a $CO_2$ stream; and d) passing the second effluent stream to an ammonia synthesis zone operated at conditions to produce ammonia.

9. The method of claim 8 wherein the carboxydotrophic bacterium is selected from the group comprising *Moorella, Clostridium, Ruminococcus, Acetobacterium, Eubacterium, Butyribacterium, Oxobacter, Methanosarcina, Methanosarcina*, and *Desulfotomaculum*.

10. The method of claim 9 wherein the carboxydotrophic bacterium is *Clostridium autoethanogenum*.

* * * * *